United States Patent
Chattopadhyay et al.

(10) Patent No.: US 11,596,763 B2
(45) Date of Patent: Mar. 7, 2023

(54) PATIENT TAILORED SYSTEM AND PROCESS FOR TREATING ASD AND ADHD CONDITIONS USING MUSIC THERAPY AND MINDFULNESS WITH INDIAN CLASSICAL MUSIC

(71) Applicants: Indrani Chattopadhyay, Avon, CT (US); Shankar Mukherjee, Avon, CT (US)

(72) Inventors: Indrani Chattopadhyay, Avon, CT (US); Shankar Mukherjee, Avon, CT (US)

( * ) Notice: Subject to any disclaimer, the term of this patent is extended or adjusted under 35 U.S.C. 154(b) by 800 days.

(21) Appl. No.: 16/531,347

(22) Filed: Aug. 5, 2019

(65) Prior Publication Data

US 2021/0038857 A1    Feb. 11, 2021

(51) Int. Cl.
*A61M 21/00* (2006.01)
*G10H 1/00* (2006.01)
*A61B 5/16* (2006.01)

(52) U.S. Cl.
CPC .............. *A61M 21/00* (2013.01); *A61B 5/168* (2013.01); *G10H 1/0008* (2013.01);
(Continued)

(58) Field of Classification Search
CPC .............................................. A61M 21/00–02
See application file for complete search history.

(56) References Cited

U.S. PATENT DOCUMENTS

| | | | | |
|---|---|---|---|---|
| 3,855,998 | A * | 12/1974 | Hidalgo-Briceno | A61M 21/00 600/545 |
| 2015/0297109 | A1* | 10/2015 | Garten | A61B 5/316 600/28 |
| 2016/0055420 | A1* | 2/2016 | Karanam | A61B 5/7246 700/52 |

OTHER PUBLICATIONS https://pilu.in/index.html ("Raga Music Therapy"). (Year: 2019).*
(Continued)

*Primary Examiner* — Thaddeus B Cox (57) ABSTRACT

A method, system and processes to develop a patient tailored music therapy based on Indian Classical Music compositions to treat ASD (Autistic Spectrum Disorders) and ADHD (Attention Deficit Hyperactivity Disorder) is described. According to this present invention there is provided a method to develop a tailored music therapy for treating patients suffering from ASD (Autistic Spectrum Disorders) and ADHD (Attention Deficit Hyperactivity Disorder) based on the patient's response and a system to measure response of the patient to music therapy and mindfulness inputs. This invention comprises of a process to determine suitable Indian Classical Music compositions playlist for use in treating the patient (FIG. 1) followed by further tuning of the selections allowable note levels, ramp up and ramp down times to and from allowable note levels, melody hold times and rhythm pattern selection to develop an optimum waveform (FIG. 2) all based on measuring the patient response using a multiple input—physical movement, audio and brain wave response measurement system (FIG. 3) or thru visual observations. The invention also provides a process to determine daily therapy and mindfulness time and a process for monthly music therapy and mindfulness tailoring. The invention also provides a system (FIG. 3) to measure patient response to the music therapy and mindfulness, which can be used in conjunction with or in place of visual observations. In this invention the patient starts off with a therapy and mindfulness tailoring session where a playlist of Indian Classical Music Raga compositions is first developed, selected based on the patient's response as measured by the system provided in FIG. 3 or thru visual observations. Then patient specific optimum note level, beat rhythm pattern and rhythm pattern frequency, ramp up to and down times from (Continued)

DETERMINATION OF INDIAN CLASSICAL MUSIC COMPOSITIONS (RAGAS) TO BUILD UP THE MUSIC THERAPY AND MINDFULNESS PLAYLIST optimum note levels are determined based on the patient's response to create a waveform (FIG. 2). The playlist selections are then modified manually or by a computer program using the waveform parameters and when played to the patient elicits a Calm Range Response pattern defined by a state of stimulated mindfulness but not falling asleep characterized by specific range of motion, audio or brain wave response unique to the patient. The specific pieces of the waveform are derived by varying waveform parameters and measuring the response of the patient (FIGS. 4 A, B, C, D) using the response measuring system (FIG. 3) or thru visual observations. The invention also describes a process to develop daily listening period duration (FIG. 5). The invention describes a process used to develop a tailored therapy and mindfulness regimen tuned to the patient using response collected over a specific period of time (FIG. 6). The invention further describes a system and apparatus which dynamically measures multiple inputs—movement, voice and brain wave response of the patient in response to the music therapy and mindfulness playlist modified by the therapy and mindfulness waveform manually or automatically by software, and a software dashboard and database which collects data across a period of time and can show progress of patient during exposure to music therapy and mindfulness (FIG. 3). The invention results in a music therapy tailored to the patient.

9 Claims, 11 Drawing Sheets

(52) U.S. Cl.
CPC .............. *A61M 2021/0027* (2013.01); *A61M 2205/3375* (2013.01); *A61M 2230/10* (2013.01); *A61M 2230/63* (2013.01); *G10H 2210/161* (2013.01); *G10H 2210/315* (2013.01); *G10H 2210/341* (2013.01); *G10H 2220/376* (2013.01)

(56) References Cited

OTHER PUBLICATIONS https://www.medindia.net/patients/patientinfo/raga-therapy-for-healing-mind-and-body.htm ("Raga Therapy for Healing Mind and Body," Lakshmi Gopal, Nov. 2018). (Year: 2018).*
http://mysorevadiraj.com/portfolio/carnatic-ragas-its-benefits/ ("Music Therapy with Indian Ragas & its Benefits on human body & mind", Mysore Vadiraj, Sep. 2016). (Year: 2016).*

\* cited by examiner

FIG 1. DETERMINATION OF INDIAN CLASSICAL MUSIC COMPOSITIONS (RAGAS) TO BUILD UP THE MUSIC THERAPY AND MINDFULNESS PLAYLIST

FIG. 2 OPTIMIZED THERAPY AND MINDFULNESS WAVEFORM.

FIG. 3 MUSIC THERAPY AND MINDFULNESS RESPONSE MEASUREMENT SYSTEM

FIG. 4A   DETERMINATION OF ALLOWABLE NOTE LEVEL L2

FIG. 4B  DETERMINATION OF RAMP UP TIME T2 FROM NOTE LEVEL L1 TO L2

FIG. 4C DETERMINATION OF MELODY HOLD TIME (T3) AT NOTE LEVEL L2

FIG. 4D   DETERMINATION OF MELODY RAMP DOWN (T4)

FIG. 4E   RHYTHM PATTERN SELECTION – KAHARBA (8 BEATS) OR EK TAAL (12 BEATS) OR TEEN TAAL (16 BEATS)

FIG. 4F  RHYTHM PATTERN FREQUENCY PER MINUTE (BEATS PER MONTH) DETERMINATION

FIG. 5  DETERMINATION OF DAILY THERAPY AND MINDFULNESS TIME

FIG. 6 MONTHLY MUSIC THERAPY AND MINDFULNESS TAILORING

PATIENT TAILORED SYSTEM AND PROCESS FOR TREATING ASD AND ADHD CONDITIONS USING MUSIC THERAPY AND MINDFULNESS WITH INDIAN CLASSICAL MUSIC

BACKGROUND OF THE INVENTION

1. Field of the Invention

The present invention relates generally to music therapy and mindfulness for treating patients with ASD (Autism Spectrum Disorder) and ADHD (Attention Deficit Hyperactivity Disorder). More particularly this invention relates to creating a method to measure response of a patient to music therapy and mindfulness inputs, developing processes to create a music therapy and mindfulness input waveform and developing a patient tailored music therapy and mindfulness regimen based on Indian Classical Music Compositions (Ragas).

Current approaches to treating autism use a complex combination of drugs to treat symptoms such as anxiety, depression, OCD etc. Also, other drugs have often to be prescribed to combat the side effects of the primary drugs. These approaches do not treat the core behavior issues which are attributed to autism such as communication, repetition and social interaction. Music therapy and mindfulness offers alternate and more importantly a noninvasive method to treating both the behavior issues and symptoms associated with autism.

2. Prior Art

A method for composing music to improve individuals ultradian and circadian chronobiological rhythms using vocal incented language elements based on pre-verbal communication such as lullabies used between mother and babies in pre-verbal communications has been described in prior art. This method described in US Patent 20140249358A1 also incorporates changing tempo and volume and including a frequency spectrum in the music of the rhythms to interact with an individual's ultradian and chronobiological rhythm.

A method has been disclosed for re-habilitation of a patient having a physical impairment by providing music therapy given by a method which includes receiving biometric data from the patient regarding repetitive movements of the patient, analyzing the biomechanical data and making the patient perform repetitive movements in conjunction with the music. In this method described in US Patent application US20170296116A1, biomechanical data is received from the patient regarding repetitive movements of the patient and determining a baseline condition, determining a baseline music beat tempo having a constant frequency corresponding to the patients baseline condition, making the patient perform repetitive movements at the baseline beat tempo, analyzing the biomechanical feedback from the patient and changing the beat tempo based on a "entrainment parameter" and determining whether a goal beat tempo has been reached. a baseline condition and making changes to the tempo to ascertain whether a goal music tempo has been reached.

A method has been disclosed in US Patent 20100191037A1 where a music therapy is used in combination with cancer therapy. In this disclosure the mood of the patient is altered from an initial state to a target mood by exposing the patient to a playlist, selecting a music to start based on the mood of the patient and then changing progressively to songs in the playlist with either higher beats or lower beats depending on the starting mood of the patient till the patient reaches a target mood.

SUMMARY

A method, system and processes to develop a patient tailored music therapy and mindfulness based on Indian Classical Music compositions to treat ASD (Autistic Spectrum Disorders) and ADHD (Attention Deficit Hyperactivity Disorder) is claimed. This invention comprises of a process to determine suitable Indian Classical Music compositions playlist for use in treating the patient, followed by further tuning of the selections allowable note levels, ramp up and ramp down times to and from allowable note levels, melody hold times and rhythm pattern selection to develop an optimum waveform (all based on measuring the patient response using a multiple input—physical movement, audio and brain wave response measurement system or thru visual observations. The invention also provides a process to determine daily therapy and mindfulness time and a process for monthly music therapy and mindfulness tailoring. The invention also provides a system to measure patient response to the music therapy and mindfulness, which can be used in conjunction with or in place of visual observations. The invention also describes the building of an optimum therapy and mindfulness waveform unique to and tuned to the patient's needs.

DETAILED DESCRIPTION OF THE INVENTION

Research on autistic children by the inventor using certain specific Indian Classical Music compositions (Ragas) has shown these compositions (Ragas) to have a beneficial effect on mindfulness. Indian ragas have different beat patterns and tempos interspersed in the compositions. Some Raga compositions were observed to have calming effects, whereas others created restlessness in some of the children. Tempos and beat patterns also induced different states in the children. Research has shown that beneficial effects are obtained with modification of rhythm pattern frequency, tempos, note levels, hold times at certain note levels. Beneficial effects were also observed for specific listening times and how tempo and note levels are changed during the therapy and mindfulness session. The therapy and mindfulness composition (Raga) becomes different from the compositions (Ragas) which are normally performed live or recorded in albums.

Research also showed that note levels, rhythm pattern frequencies, hold, ramp up and ramp down times (how quickly note levels are changed from one level to another) (FIG. 2) could be tailored for individual child patients in addition to specific raga composition selections. Research conducted by the inventors showed that the child patient exposed to the therapy and mindfulness exhibits reaction to the music with for example type and pattern of movements, speech indicators, following along with the music by humming and snapping fingers with the beat. Indian Classical Music compositions have mainly three types of major rhythm patterns or patterns with certain number of beats. The three rhythm patterns are Kaharba (8 beat pattern), Ek Taal (12 beat pattern) and Teen Taal (16 beat pattern). Research has shown Ek Taal and Teen Taal to have beneficial effects on most patients. The three rhythm patterns have been used to construct the optimized waveform, though other rhythm patterns can also be used. The process described in this invention starts out with concert type 14 rhythm patterns per minute type of pattern frequency which is then modified to each patients' requirements. The right music composition, rhythm pattern, rhythm pattern frequency, note levels, ramp up and ramp down times to and from optimum note levels is herein defined as "calm range response pattern" which characterizes the target mindfulness for therapy and mindfulness which can be specific to the child/patient.

In view of the prior art, it is an object of the current invention to provide a process for treating children and patients with autism which can be dynamically tailored to the child's/patient's needs. This approach uses Indian Classical Music compositions (Ragas), a method using visual observations to manually measure or sensors to automatically measure response of the child or patient to the therapy and mindfulness to tune the music therapy and mindfulness to the child's/patient's needs, a computer-based program (computer or smartphone) which in conjunction with a data acquisition system can collect sensor input, select specific ragas based on sensor input measuring the child patient's response, alter the music therapy and mindfulness composition note levels, rhythm beat frequencies based on sensor input which when played to the patient creates a state of optimum mindfulness defined as calm range response pattern which if elicited in the child for specific periods of time daily will result in a tailored therapy and mindfulness for the child.

According to the first aspect of the invention there is provided a process and system for music therapy and mindfulness to treat children with ASD (Autistic Spectrum Disorders) and ADHD (Attention Deficit Hyperactivity Disorder). The process consists of exposing the child patient to a set of Indian Classical Music Compositions (known as Ragas), determining the right raga music compositions which are optimum for the child determined by the child exhibiting the "calm range response pattern", creating a playlist from the selected raga music compositions, changing either using the computer program described herein or manually, the note levels, times to ramp up to and ramp down from optimum note levels and beat frequency of the raga music compositions in the playlist to create an optimized therapy and mindfulness waveform processed playlist for sustained therapy and mindfulness, determining daily therapy and mindfulness time optimized for the child, determining a monthly playlist, a monthly modified waveform which can then be used to modify the playlist and daily listening time modification designed to capture the child's attention and keep the child focused on the therapy and mindfulness and address any deterioration of child's mindfulness caused by boredom with the previous therapy and mindfulness regimen. The first aspect of the invention also discloses a system for evaluating if the child has reached the "calm range response pattern" using sensors attached to the child to capture movement response and with or without a EEG sensor capturing brainwave response, microphone capturing auditory response from the child patient, a computer system which could be a conventional computer with processors with a data acquisition system or a smartphone/tablet with built in data acquisition to capture the data, a software program developed to analyze the data captured in response to the Indian Classical Music composition based music therapy and mindfulness which could be a program for a conventional computer or an app on a smartphone to analyze the data at a pre-determined frequency and present compiled results through a dashboard on the conventional computer or using an app on a smartphone/tablet, a system to upload the music therapy and mindfulness response data from the computer or smartphone/tablet to a data cloud for storage using a WIFI or Cellular Connection with the option of also storing the data locally on the computer or smartphone/tablet, a dashboard which displays the results computed by the software program described in this aspect of the invention or smartphone/tablet app to monitor and track progress of the child during the course of the therapy and mindfulness and indicate when a therapy and mindfulness modification is required. The system also uses a medium to store the Indian classical music composition (raga) playlist, Indian classical music composition (raga) music library for the therapy and mindfulness. The system also uses a music system or smartphone/tablet to play the playlist raga compositions to the child and patient. Visual observations can also be used to determine if the child and patient has reached target "calm range response" in response to the music therapy.

In the second aspect of the invention there is disclosed that a music library can be created composed of Indian Classical Music compositions (ragas) which when tailored to the patient's needs in the form of a optimized therapy and mindfulness waveform (FIG. 2) and played to the patient can bring an autistic or ADHD patient to a "calm range response pattern" which if sustained over a period of time can reduce symptoms of autism such as but not limited to repetitive movements, restlessness, social skill challenges and speech.

Figure 2:
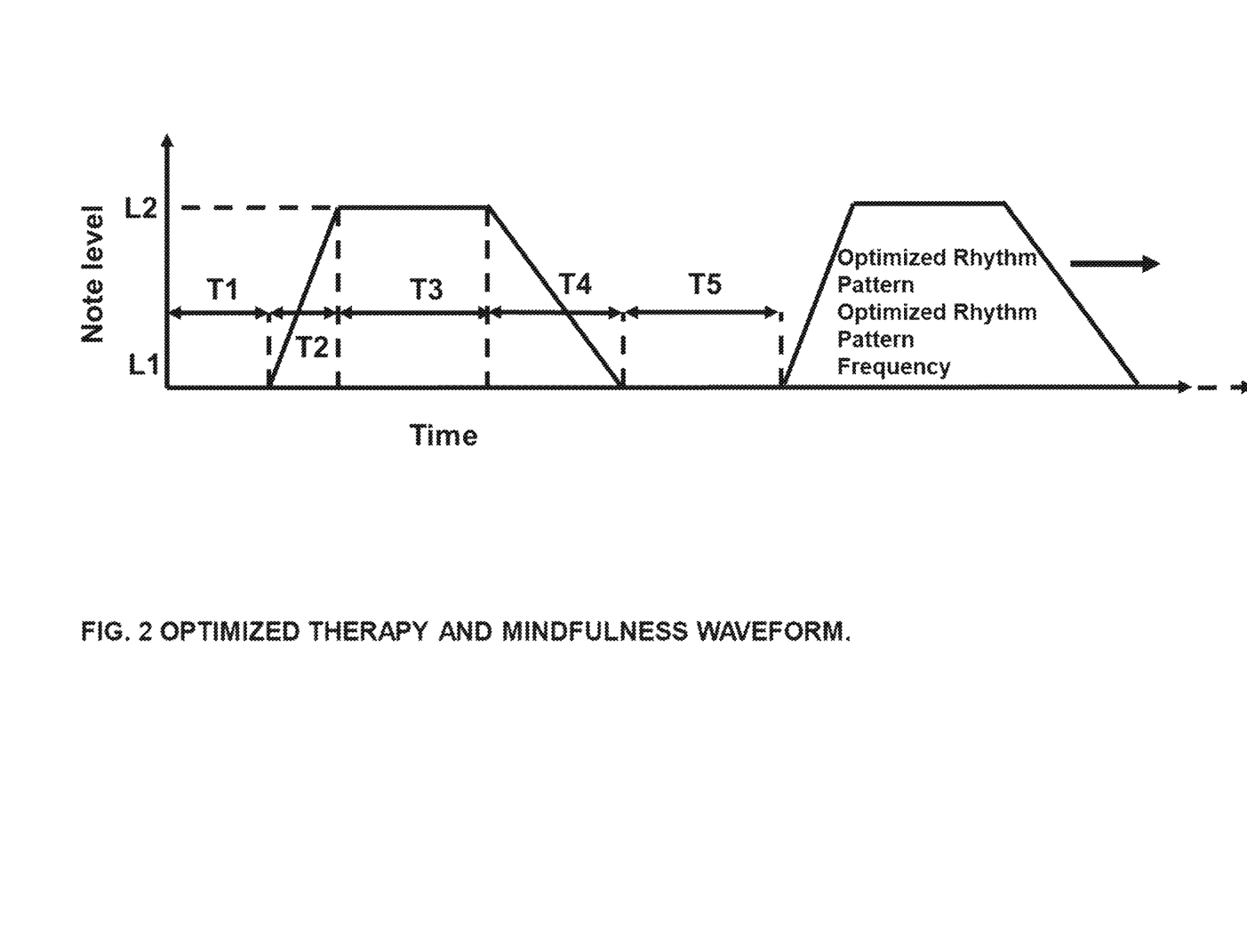
FIG. 2 is a drawing which shows the optimized music therapy and mindfulness waveform and its components.

In the third aspect of the invention there is disclosed that Indian Classical Ragas can be tailored to a patient's needs to get the patient to a beneficial "calm range response pattern" by altering rhythm pattern frequency, note levels, ramp up and ramp down times to and from optimum note levels to create an optimized therapy waveform (FIG. 2). The therapy waveform parameters are then used to modify the playlist automatically using the computer program described herein or manually. The modified playlist when played to the patient over specific sustained period of music therapy elicits "calm range response". The music waveform approach has primarily used Indian Classical Music Raga compositions, but the approach can cover all types of music compositions such as but not limited to Western Classical Music, soft rock, pop etc.

In the fourth aspect of the invention there is disclosed a "calm range response pattern" exhibited by the patient defined as a state of stimulated mindfulness but not falling asleep characterized by specific range of motion, audio or brain wave state unique to the patient which is a weighted average of movement frequency, speech response such as humming and with or without brain waveform response. This "calm range response pattern" can vary from patient to patient and is specific to the individual patient. The weighting method is tuned to the patient. Other data aggregating methods other than weighting can also be used. In the beginning of the therapy an initial "calm range response pattern" is determined thru visual observations and then correlating the sensor data corresponding to when visual observation indicates calm range response pattern is reached. This set of observations and corresponding measurements can be unique to each patient. The process can also be automated thru using the sensor measurements and having a software program determine when response variations reach a stable state which can be unique to each patient.

Figure 3:
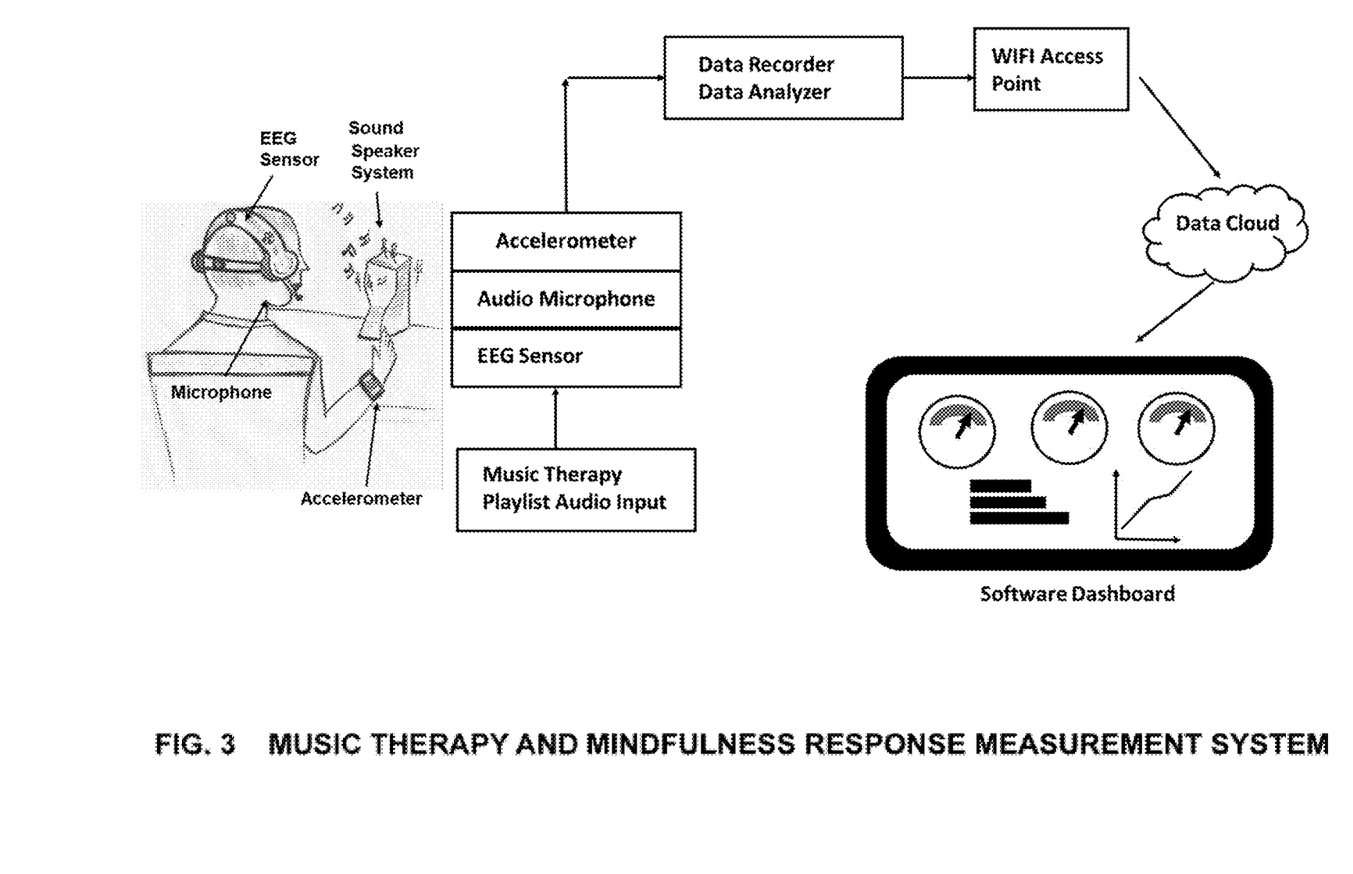
FIG. 3 is a drawing which shows the music therapy and mindfulness response measurement system.

In the fifth aspect of the invention shown in FIG. 3 there is provided a system for measuring the response to the tailored music therapy for evaluating if the child has reached a "calm range response pattern" in response to the tailored music therapy. In this system sensors for capturing response data as the patient listens to the waveform modified music therapy playlist such as but not limited to accelerometer, audio microphones and EEG sensors are attached to the child during therapy sessions. The accelerometer and audio microphone could also be combined in the form of a "smartphone" or tablet having these sensors and attached to the patient. The system disclosed also has a data recorder which captures the data. The data recorder can be a separate system or can be integrated into a smartphone or tablet type of device. The response data collected from the patient is aggregated using a weighted algorithm by a data analyzer. The aggregated data in the beginning of the therapy is correlated with physical observations in in the initial part of the process to define Calm range response Pattern for the specific patient which then becomes the target calm range response state. The ongoing data measurements continuously compare the acquired data to the aggregated sensor measurements data corresponding to the calm range response pattern to ensure calm range response pattern is being reached or maintained and measure any deviations from target "calm range response pattern" measurements of the patient. Deviations from "calm range response pattern" measured are used to trigger changes in the waveform and therapy exposure time periods and duration. The data analyzer can be a hardware with firmware performing the data acquisition and computation or a software on a computer, a cloud-based software or an app on a smartphone. The data analyzer uploads the aggregated and raw data using an internet connection which can be a WIFI connection as shown in FIG. 3 or can be a hard wired ethernet connection. A display dashboard software then downloads the data from the data cloud and displays the patient response measurements in a dashboard. The software for data collection, data analysis and dashboard can be separate programs or a single program on a conventional computer or a smartphone or tablet-based app. The storage of the data can be local on a computer, on a tablet or on a data cloud system. The music therapy playlist is played on a sound system or a smartphone or a handheld tablet.

Figure 1:
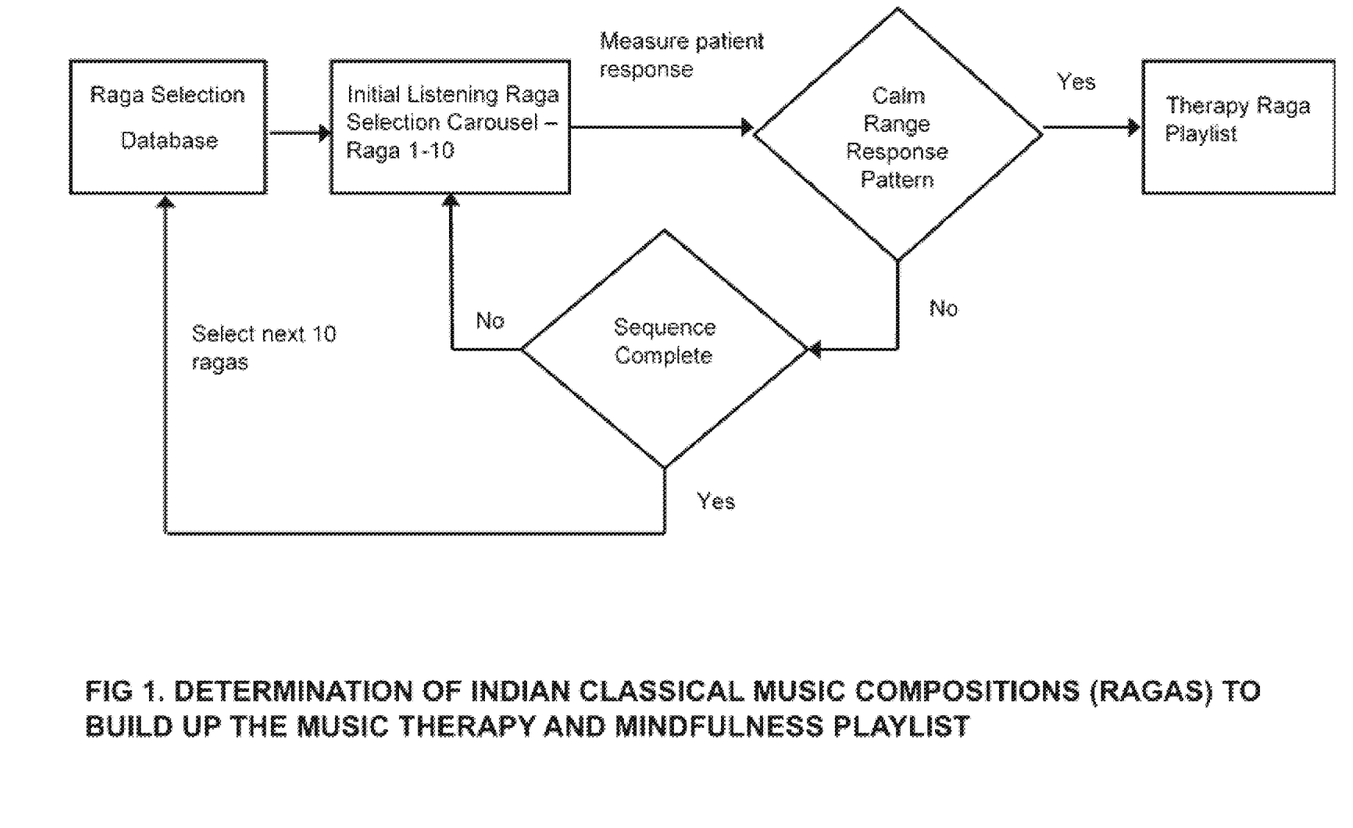
FIG. 1 describes method and process to determine the Indian Classical Music compositions which comprise the playlist for the music therapy and mindfulness.

In the sixth aspect of the innovation there is described a process shown in FIG. 1 for selecting the Indian classical music compositions (ragas) making up the playlist. The process starts with selecting an initial set of 10 ragas based on initial observations of the patient's symptoms. The playlist is played to the patient and the patient's response is measured quantitatively using the system shown in FIG. 3 and disclosed as the fifth aspect of the innovation or qualitatively thru visual observations. The patient's response is measured and compared against the patient's calm range response pattern. If the playlist generates a calm range response pattern from the patient, then the playlist is finalized as the therapy playlist. If the selection set does not generate a calm response pattern, then the playlist compositions are replaced by the next 10 ragas. The process is repeated until a calm response pattern is generated and the playlist is then finalized as the starting music therapy playlist.

Figure 4A:
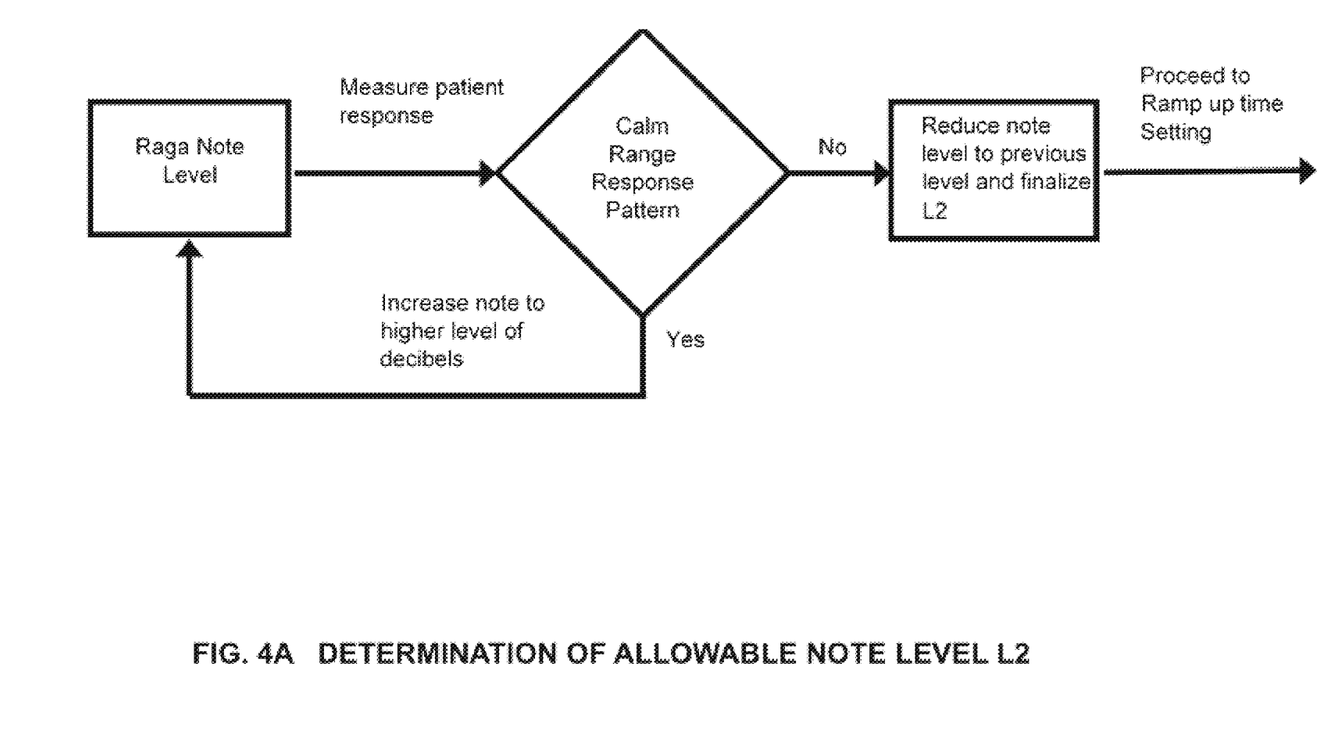
FIG. 4A shows the method to determine the allowable note level L2 of the music therapy and mindfulness waveform.
Figure 4B:
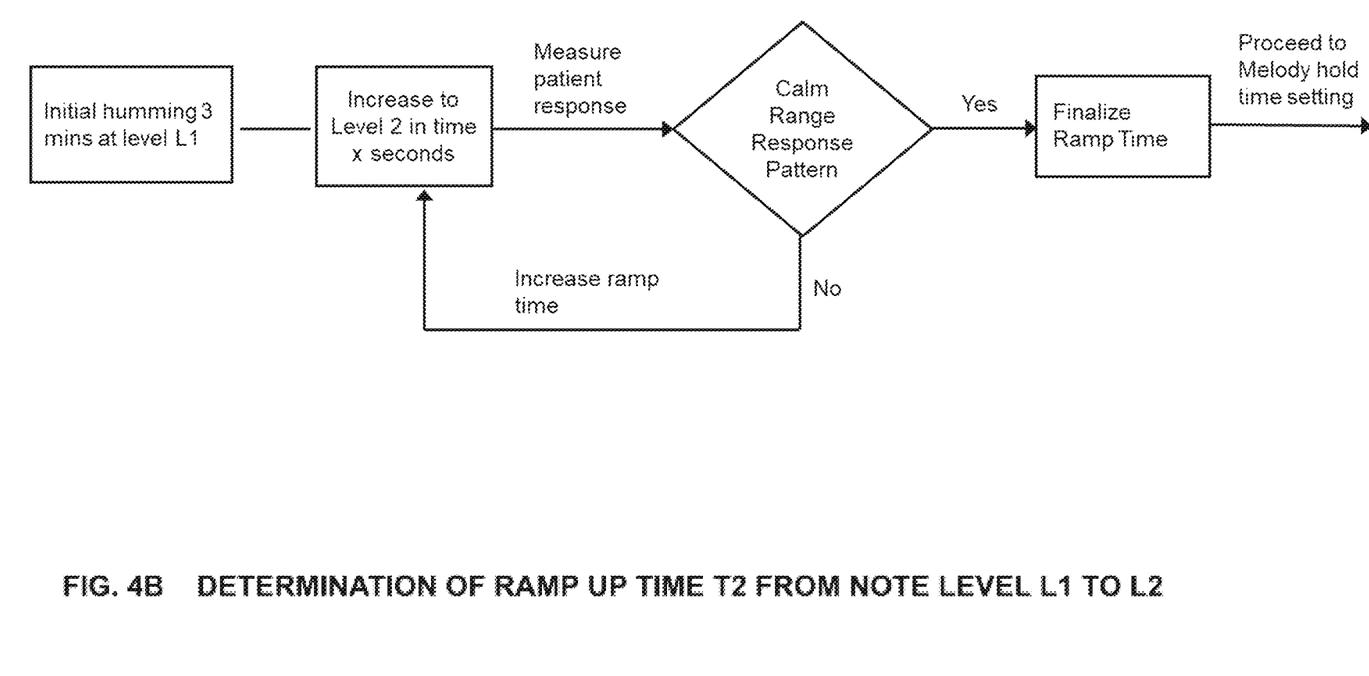
FIG. 4B shows the method to determine the ramp up time of the optimized music therapy and mindfulness waveform.
Figure 4C:
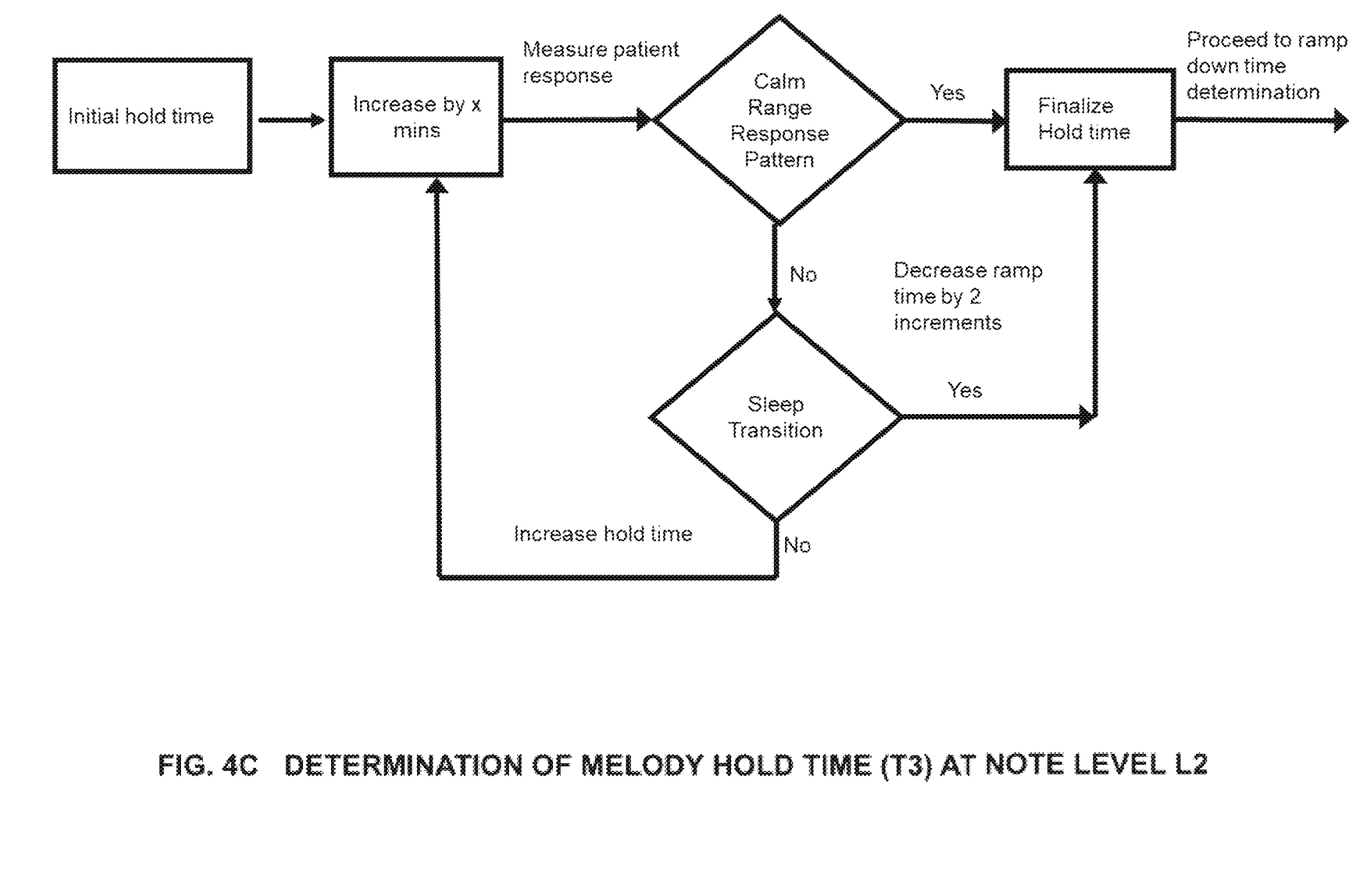
FIG. 4C shows the method to determine the melody hold time at allowable note level of the music therapy and mindfulness waveform.4
Figure 4D:
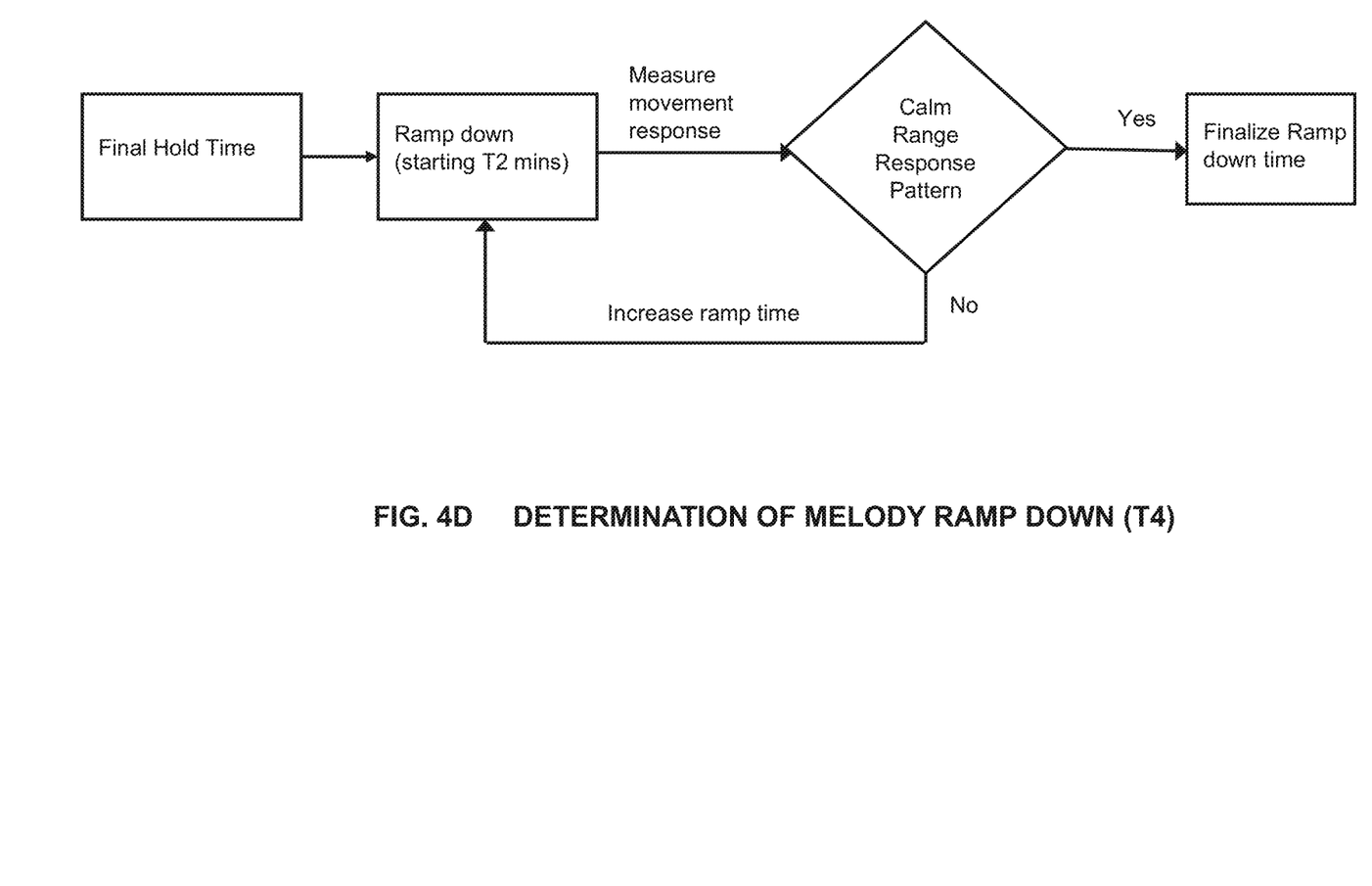
FIG. 4D shows the method to determine the ramp down times from allowable note level of the music therapy and mindfulness waveform
Figure 4E:
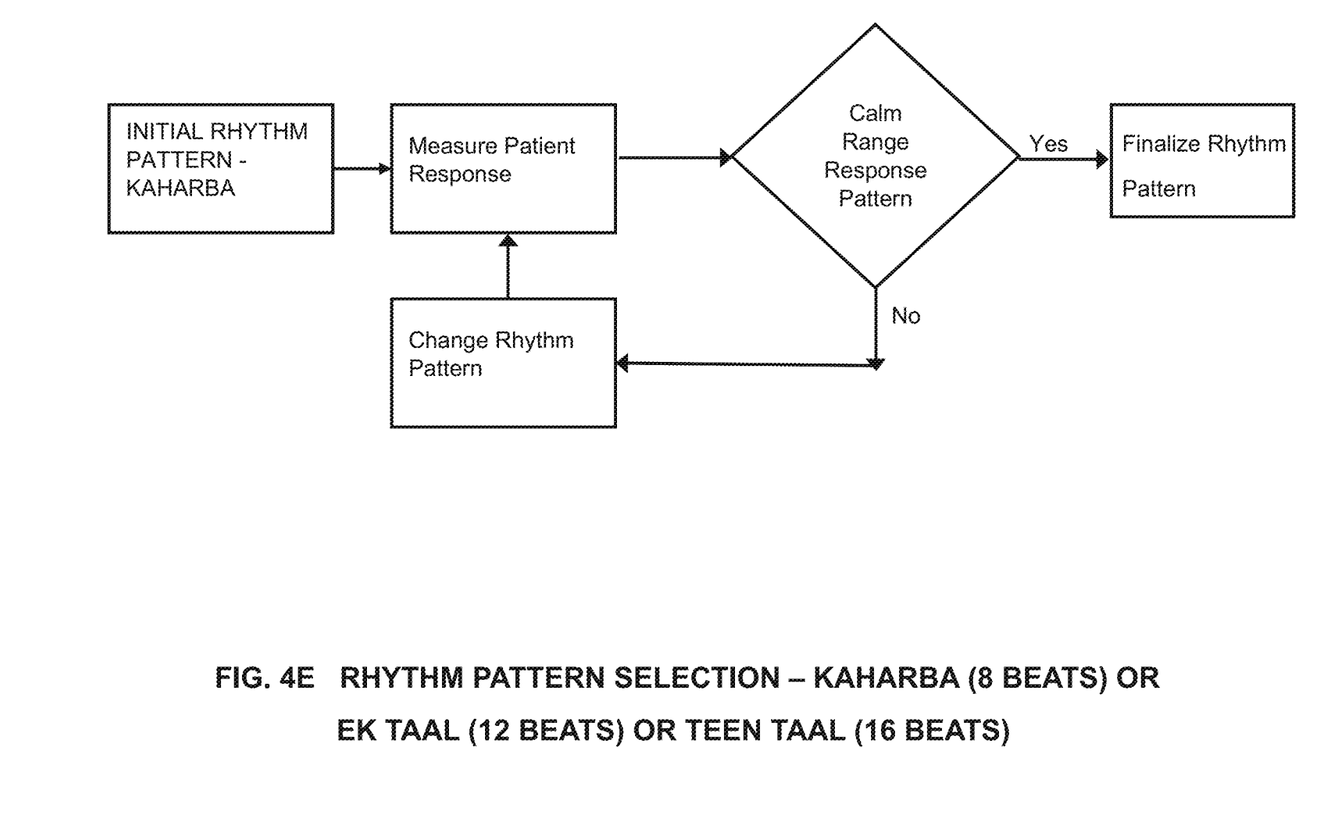
FIG. 4E shows the method to select the rhythm pattern of the optimized therapy and mindfulness waveform.
Figure 4F:
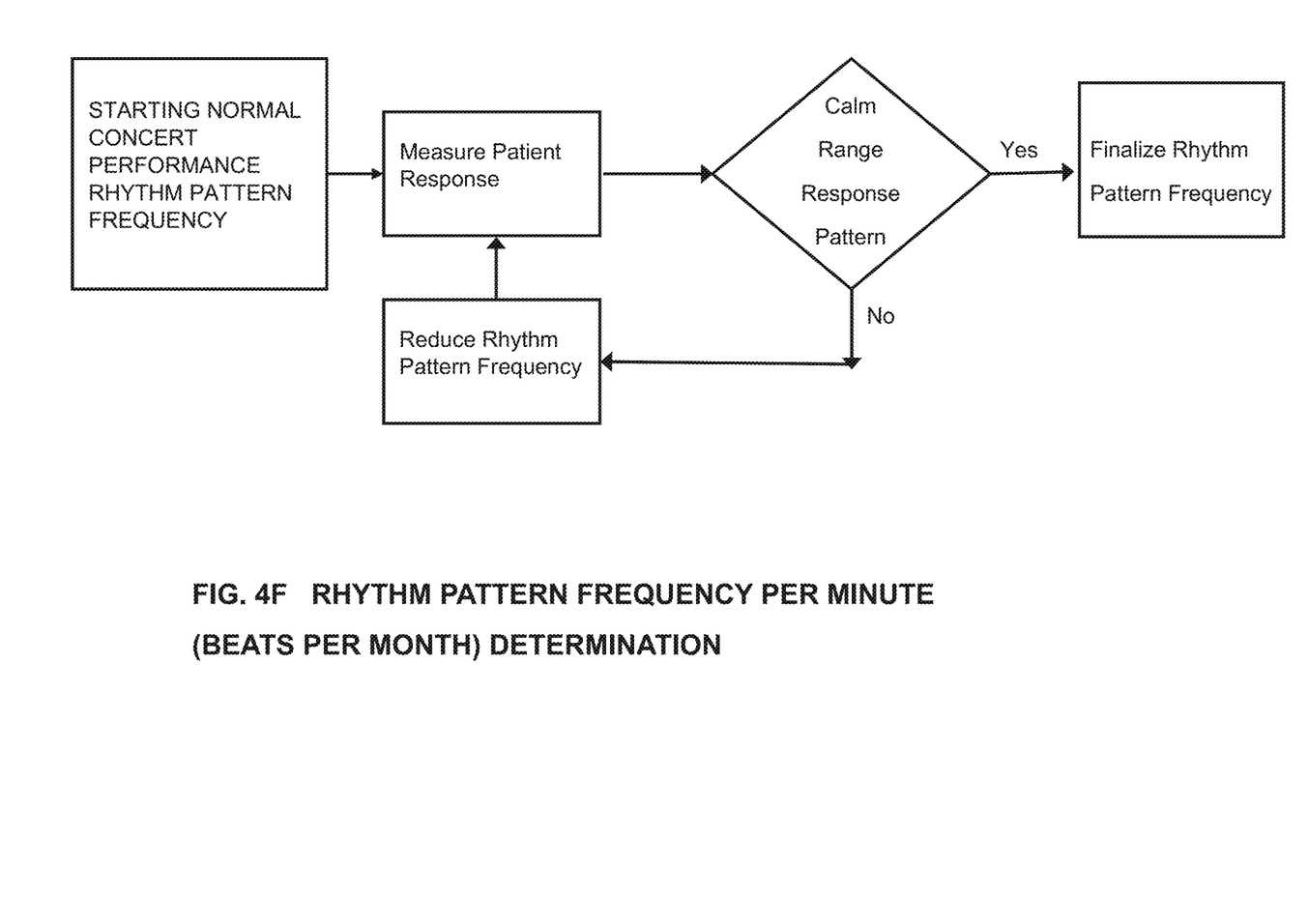
FIG. 4F is a diagram which outlines the method to determine the rhythm pattern frequency per minute of the optimized therapy and mindfulness waveform.

In the seventh aspect of the innovation there is described a process for determining the various parts of the optimized therapy waveform with associated rhythm pattern and rhythm pattern frequency. The process is shown in FIGS. 4A, 4B, 4C and 4D. After selection of the playlist of Indian Classical Music compositions (ragas), parameters such as note levels, ramp up and ramp down times to and from allowable note levels (L2 in FIG. 2) and hold times at allowable note levels L2 decibels are determined to create the optimized waveform in FIG. 2. The Indian classical music compositions (ragas) in the playlist are altered manually thru actual singing and recording the altered Indian Classical Music composition (raga) or automatically thru a software program. In this tuning process, in the first part of the process, shown in FIG. 4A, the note level of the Indian classical music compositions (ragas) in the playlist is optimized to produce a calm range response pattern. In this part of the process, as shown in FIG. 4A, the Indian classical music compositions (ragas) in the playlist are played to the patient and the note levels are steadily increased starting from a soft humming (Level L1 in FIG. 2) in steps. At each step of the increase the patient's response is measured qualitatively thru visual observations or quantitatively using the system shown in FIG. 3. If the current note level does not cause the patient response to shift from calm response state, then the note level is increased by 1 step to the next step and the process is repeated. Notes are increased till the response pattern shifts away from the calm response pattern, then the note level is decreased to the previous step and finalized and is characterized by level L2 decibels (FIG. 2). At each note increase step the response of the patient is observed. In the second step described in FIG. 4B, a process is described to determine the ramp up time T2. This process starts with the ragas in the playlist played to the patient by initial soft humming at note level L1 for time T1. Then the note level of the playlist is increased rapidly to note level L2 to elicit a response not at calm response state and the patient's response is measured qualitatively thru visual observations or quantitatively using the system shown in FIG. 3. Then the ramp process of increasing the note levels of the playlist is repeated but at 1 step slower and the modified ragas in the playlist are played to the patient and the patient's response is measured. If the patient response is not at calm response, then ramp up time is lengthened, and the process is repeated until the patient reaches calm response state. This optimized ramp up time is finalized as ramp up time T2 (FIG. 2). The next piece of the process determines the hold time T3 at optimum note level L2 (FIG. 2). This process is shown on FIG. 4C. The process shown in FIG. 4C starts with the ragas in the playlist played to the patient with an initial hold time at note level L2 chosen after observing the patient. The hold time is then increased by X mins (the step change is dependent on patient observation). The patient's response is measured qualitatively thru visual observations or quantitatively using the system shown in FIG. 3. The response is checked to see if the patient has reached calm response state, if the state reached is not calm response state, then an additional check is performed to see whether the patient is transitioning to a sleep state. If the patient is not reaching sleep state, then the hold time at note level L2 is increased and the process is repeated. If it is observed that the patient has reached calm response pattern, then an additional check is performed to see if the patient is transitioning to a sleep state. If the patient is not transitioning to sleep state, then the hold time is again increased and the ragas in the playlist are played to the patient. If the patient is transitioned to sleep state after calm state response is achieved, then the hold time is decreased by 2 increments and the hold time is decreased by 2 increments and this decreased hold time level is finalized as hold time T3 (FIG. 2). The next part of determining the optimized therapy waveform is determining the ramp down time T4. The process is shown in FIG. 4D. In this process after final hold time is determined, melody is ramped down using the final ramp up time T2 mins as a baseline. The response of the patient is measured qualitatively thru visual observation or quantitatively using the system shown in FIG. 3. If the response is not Calm Range Response Pattern, then the ramp down time is increased from final hold time T3 and the process is repeated till a calm range response pattern is maintained. This ramp down time is then finalized as time T4 mins. If the ramp down time using the baseline time T2 mins results in maintaining the calm range response pattern, then the ramp down time T4 mins is the same as ramp up time T2 mins. The next part of determining the optimized waveform is to select the rhythm pattern most suitable for the patient. The process of selecting the optimum waveform is shown in FIG. 4E. In this process the patient is initially exposed to raga composition in the playlist using one of the three rhythm patterns Kaharba (8 beats) or Ek Taal (12 beats) or Teen Taal (16 beats). The response of the patient is measured qualitatively thru visual observation or quantitatively using the system shown in FIG. 3. If the response is not Calm Range Response Pattern, then the process is repeated using the other two rhythm patterns. If the response obtained from the patient is Calm Range response Pattern, then the rhythm pattern is finalized. The final part of determining the optimized waveform is determining rhythm pattern frequency also known as the beat frequency. The process starts with playing the Indian Classical Music compositions in the playlist using the optimum rhythm pattern and starting with normal concert performance style 12 beats per minute. The response of the patient is measured qualitatively thru visual observation or quantitatively using the system shown in FIG. 3. If the response is not Calm Range Response Pattern, then the beat frequency is reduced, and the response of the patient is measured. When the beat frequency generates a Calm Range Response from the patient then that frequency is finalized as the optimized beat frequency.

Figure 5:
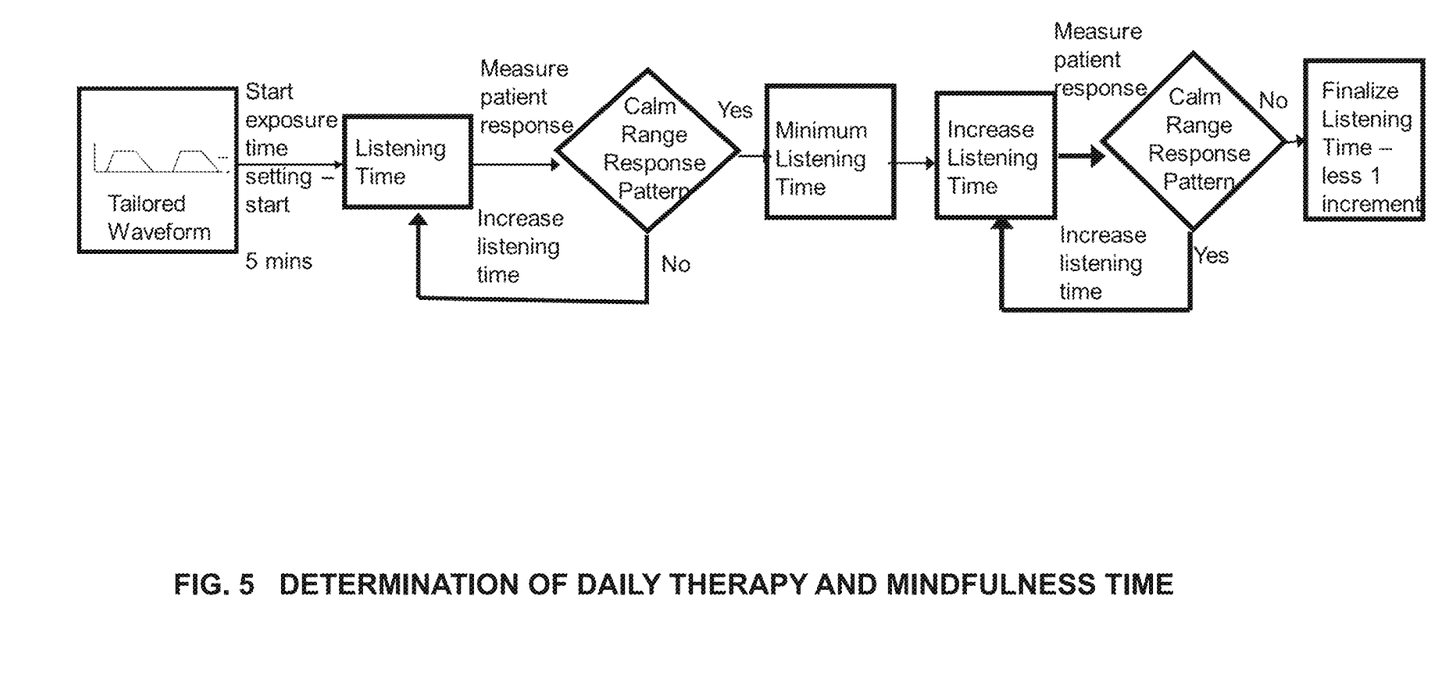
FIG. 5 shows the method to determine the daily music therapy and mindfulness time.
Figure 6:
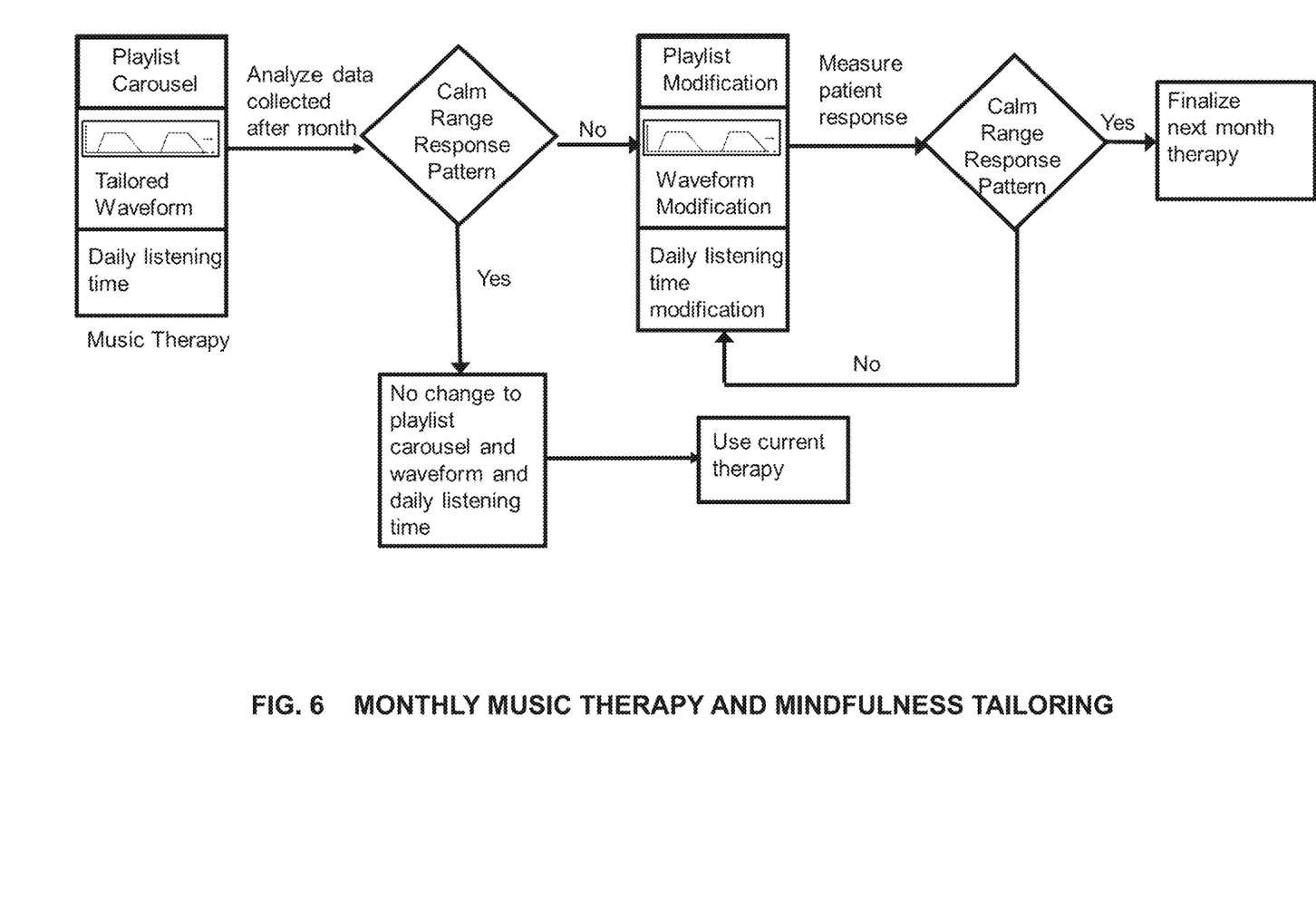
FIG. 6 shows the method to tune and tailor the music therapy and mindfulness based on the response of the patient.

In the eighth aspect of the innovation, there is described a process shown in FIG. 5 for determining the daily therapy time tailored for the patient. The process starts with exposing the patient to the Indian classical music composition (raga) playlist modified by the tailored waveform for 5 mins. The response of the patient is measured qualitatively thru visual observation or quantitatively using the system described in FIG. 3. If calm range response pattern is observed the listening time is finalized as the minimum listening time. If the calm range response pattern is not obtained, then the listening time is increased in steps of 5 mins or a time increment suitable for the patient based on observation and the process is repeated till a calm range response pattern is obtained. This becomes the minimum listening time. The listening time is then steadily increased in steps of 5 mins and the patient's response is measured qualitatively using visual observation or the system described in FIG. 3. If a calm range response pattern is obtained, then the listening time is increased, and the process is repeated as shown in FIG. 5. If the response deviates from the calm range response pattern, then the maximum listening time is fixed at the previous increment. This process determines the daily listening time.

In the ninth aspect of the invention, there is described a process to tailor and tune the therapy every month or within the month if deviations from calm response pattern are observed. If the same playlist, waveform and daily listening time is continued unchanged for long periods of time there is a chance that this may induce boredom or impatience. This approach allows for altering the playlist, waveform and daily listening time to keep tuning the therapy to the patient's evolving needs. Data is collected manually or automatically using system described in FIG. 3 over the month or for a shorter duration of time when deviations are observed. If no deviations from Calm range response pattern are observed and calm ranges response pattern has been maintained, then no changes are made to the therapy. If deviations are observed from the calm range response pattern then the process for determining the playlist, waveform, and daily therapy time is repeated following processes in the first nine aspects of the innovation.

What is claimed is:

1. A method to develop a music therapy using Indian classical music compositions (Ragas) for treating patients with ASD (autism spectrum disorders) and ADHD (attention deficit hyperactivity disorder) disorders tailored to their specific needs, which when applied to a patient for daily periods of time results in reduction of ASD and ADHD symptoms, the method comprising:

developing a playlist/music library of Indian classical music compositions (Ragas) and tailored to an ASD or ADHD patient's needs in the form of an optimized music therapy waveform that can be played to the ASD or ADHD patient to bring the patient to a calm range response pattern;

developing the optimized music therapy waveform through modification of parameters of the waveform including note levels, rhythm pattern frequency, ramp up to optimum note levels, holds at optimum note levels and ramp down from optimum note levels of the Indian classical music compositions in the playlist/music library, based on measurements of the patient's response to the waveform, and modification of all playlist/music library compositions to match the optimized music therapy waveform;

developing a therapy parameter to characterize the calm range response pattern specific for the patient which defines a target mood and behavior of the patient due to the optimized music therapy waveform unique to the patient, including optimum physical movement, speech and brainwave response, computed by using several aggregating methods with at least one of the methods being a weighted average of the patient's response to the optimized therapy waveform including physical movement frequency, speech response and brain waveform response;

collecting data to measure the patient's response captured qualitatively using observations and using a computer implemented system for capturing the physical movement frequency, speech response and brainwave response of the patient to the optimized music therapy waveform;

combining the data into the therapy parameter to see if the calm range response pattern is obtained and to measure deviations from the calm range response pattern using multiple sensors;

transferring and storing the measured data from the multiple sensors in at least a local storage device and a data cloud, wherein the measured data can be transferred from the local storage device to the data cloud;

selecting the Indian classical music compositions (Ragas) for the playlist/music library starting with an initial set of Ragas selected based on initial observations of the patient's symptoms, having the patient listen to the initial set of Ragas and measuring the patient's response to see if the calm range response pattern is generated, iteratively replacing Ragas of the initial set with different Ragas if the calm range response is not generated until a set of Ragas which generate the calm range response pattern is found, wherein the set of Ragas which generate the calm range response pattern is finalized to be the Ragas comprising the playlist/music library;

determining parameters of the optimized music therapy waveform by:
(i) playing Ragas in the playlist/music library at an initial note level and steadily increasing the note level in small increments until a deviation is observed from the calm range response pattern in the patient, then bringing the note level to one increment below the increment at which the deviation is observed,
(ii) iterating the ramp up time by starting with a rapid increase in note levels to go from the initial note level to a final note level, checking to see if the calm range response pattern is observed and if not returning to the initial note level and slowly increasing the ramp up time in small increments until the calm range response pattern is observed in the patient, wherein the increment at which the calm range response pattern is observed is determined to be the optimal ramp up time of the optimized music therapy waveform,
(iii) determining a hold time of the optimized music therapy waveform starting with an initial hold time and then slowly increasing the hold time in increments until the calm range response pattern is observed in the patent, progressively increasing the hold time while checking to see if the patient is transitioning to a sleep state until the patient transitions to the sleep state, and determing the optimized hold time for the optimized music therapy waveform as one increment below the hold time when the patient transitions to the sleep state,
(iv) optimizing the ramp down time of the optimized music therapy waveform from the optimized hold time to the initial note level by checking to see if deviations from the calm range response pattern are observed and if observed then progressively increasing the ramp down time in increments until the calm range response pattern is observed, wherein the increment at which the calm range response pattern is observed is determined to be the optimized ramp down time of the optimized music therapy waveform,
(v) selecting an optimized rhythm pattern starting from an initial rhythm pattern, wherein the initial rhythm pattern is selected from Akhara (typical frequency of 8 beats per minute), Ek Taal (typical frequency of 12 beats per minute) and Teen Taal (typical frequency of 16 beats per minute), measuring the patient's response, and selecting each of the remaining two rhythm patterns until a rhythm pattern is determined to produce the calm range response in the patient, wherein the rhythm pattern determined to produce the calm range response to determined to be the optimized rhythm pattern of the optimized music therapy waveform and,
(vi) determining an optimized rhythm pattern frequency starting from the typical frequency of the optimized rhythm pattern measuring if the calm range response pattern is obtained at the typical frequency, and if not obtained then progressively reducing the frequency in increments until a frequency that produces the calm range response pattern in the patient is determined, wherein the frequency that produces the calm range response pattern in the patient is determined to be the optimized rhythm pattern frequency of the optimized music therapy waveform; determining a duration of a daily therapy time when the patient listens to the playlist/music library containing the Indian classical music compositions modified using the optimized music therapy waveform, starting with having the patient listen to the playlist/music library for an initial time duration, measuring the response of the patient and then progressively increasing the listening time in increments until the calm range response pattern is observed, wherein the increment at which the calm range response pattern is observed is determined to be a minimum daily therapy time, further increasing the listening time in increments until a deviation from the calm range response is observed, and finalizing the duration of the daily therapy time to be one increment below the increment at which the deviation from the calm range response pattern is observed; and tuning the music therapy to evolving needs of the patient at least monthly if deviations from the calm range response pattern are observed by re-selecting Ragas, re-determining parameters of the optimized music therapy waveform, and/or re-determining the duration of the daily therapy time to produce the calm range response pattern in the patient.

2. The method of claim 1, wherein the playlist/music library modified by the optimized music therapy waveform is played to the patient for daily periods of time resulting in reduction of ASD and ADHD symptoms.

3. The method of claim 1, wherein the computer implemented system further comprises:
sensors for capturing the patient's response when listening to the optimized music therapy waveform;
a connection from the sensors to a data recorder and an acquisition box using cables/wires or wireless methods including Bluetooth;

the data recorder for capturing patient response data;

a data analyzer that can be connected to the data recorder or integrated with the data recorder as a single unit for analyzing and aggregating the patient response data to evaluate if the calm range response state has been reached;

a storage device for storing the patient response data locally on a computer or in a data cloud;

a connection from the data recorder and data analyzer to a local storage device using wired methods and wireless methods including Bluetooth or to a data cloud using WIFI, ZigBee or cellular;

the data cloud for storage of daily and monthly patient response data; and a software program which takes the patient response data and displays a dashboard of the patient response data daily and monthly.

4. The method of claim 3, wherein the sensors are either separate sensor or are integrated into a smartphone, and wherein the sensors further comprise:

sensors measuring a movement response of the patient;
sensors to record audio of a patient response; and
sensors to measure a brainwave response.

5. The method of claim 3, wherein the computer implemented system further comprises at least one of:

a data acquisition board and box which captures a patient movement response;

a data acquisition board and box which captures a patient speech response;

a data acquisition board and box which captures patient brain wave response data;

a data acquisition system comprising a single board capturing all sensor data;

and a data acquisition system in the form of a smartphone, tablet, desktop computer, or laptop computer with integrated boards.

6. The method of claim 3, wherein the computer implemented system further comprises at least one of:

a hard drive containing patient response capturing data acquisition boards; and a smart phone or tablet equipped with a data acquisition program able to capture sensor inputs.

7. The method of claim 3, wherein patient response data is transferred in at least one of the following ways:

via Bluetooth to data acquisition boards in a computer;
to data acquisition boards in a mobile tablet or smart phone through Bluetooth;
through Bluetooth to a separate data storage device;
through Wi-Fi to data acquisition boards in a laptop computer;
through Wi-Fi to data acquisition boards in a desktop computer;
to data acquisition boards in a mobile tablet or smart phone through Wi-Fi;
through Wi-Fi to a separate data storage device;
through a cable connection to data acquisition boards in a laptop computer;
through a cable connection to data acquisition boards in a desktop computer; and
to a mobile tablet or smart phone through a cable connection.

8. The method of claim 3, wherein patient response data is transferred to a data cloud in at least one of the following ways:

using a wireless access point/portal point;
using a cellular connection; and
using a wired internet connection.

9. The method of claim 1, wherein the method is implemented in a software program on a desktop computer, a software program on a laptop computer, and/or a software program in the form of an application on a mobile device platform including a smartphone or tablet.

* * * * *